United States Patent [19]

Kelleher

[11] Patent Number: 5,618,553
[45] Date of Patent: Apr. 8, 1997

[54] METHODS AND COMPOSITIONS FOR THE MODULATION OF CELL PROLIFERATION AND WOUND HEALING

[75] Inventor: Peter J. Kelleher, The Woodlands, Tex.

[73] Assignee: Houston Biotechnology Incorporated, The Woodlands, Tex.

[21] Appl. No.: 483,795

[22] Filed: Jun. 7, 1995

Related U.S. Application Data

[63] Continuation-in-part of Ser. No. 329,366, Oct. 26, 1994, abandoned.

[51] Int. Cl.⁶ ............................................................. A61F 2/02
[52] U.S. Cl. .................................... 424/428; 424/427; 514/912
[58] Field of Search .......................... 424/78.04, 427, 424/428; 514/912

[56] References Cited

U.S. PATENT DOCUMENTS

| 4,093,709 | 6/1978 | Choi et al. ........................ 424/427 |
| 4,937,270 | 6/1990 | Hamilton et al. .................. 514/777 |
| 5,017,229 | 5/1991 | Burns et al. ...................... 106/162 |
| 5,080,924 | 1/1992 | Kamel et al. ...................... 427/2 |
| 5,246,698 | 9/1993 | Leshchiner et al. ............... 424/78.08 |

FOREIGN PATENT DOCUMENTS

| 0430539 | 6/1991 | European Pat. Off. .......... A61K 9/22 |
| 0488401 | 6/1992 | European Pat. Off. .......... A61K 9/00 |

OTHER PUBLICATIONS

Arora et al., *European Journal of Obstetrics & Gynecology*, (1994) 55:179–182.
Blandford et al., *Investigative Ophthalmology and Visual Science*, (1992) 33:3430–3435.
Diamond et al., *Fertility and Sterility* (1991) 55:389–394.
Haney & Doty, *Fertility and Sterility*, (1993) 60:550–558.
Hill–West et al., *Obstetrics and Gynecology*, (1994) 83:59–64.
Kay et al., *Ophthalmic Surgery*, (1986) 17:796–801.
Kang et al., *BioMaterials*, (1993) 14:787–792.
Lee et al., *Ophthalmology* (1987) 94: 1523–1530.
Merkli et al., *Journal of Controlled Release*, (1994) 298:105–112.
Miron et al., *Journal of Solid-Phase Biochemistry*, (1976) 1:225–236.
Mosbach, K., *Methods in Enzymology*, (ed. 1976): 118–135.
Pasternak et al., *Life Sciences*, (1976) 18: 977–982.
Pietersz, G., *Bioconjugate Chem.*, (1990) 1: 89–95.
Pouyani & Prestwich, *Bioconjugate Chem.*, (1994) 5: 339–347.
Reigel et al., *Pediatr. Neurosurg.*, (1993) 19: 250–255.
Rubsamen et al., *Archives of Ophthalmology*, (1994) 112: 407–413.
Sahin & Saglam, *Acta Obstet. Gynecol. Scand.*, (1994) 73: 70–73.
Susanna et al., *Ophthalmic Surgery*, (1994) 25: 458–462.
Wiskind et al., *Obstetrics and Gynecology*, (1993) 81: 1025–1028.
Yaacobi et al., *Journal of Surgical Research*, (1993) 55: 422–426.
Yamamoto et al., *Journal of Medical Chemistry*, (1972) 15:872–875.

*Primary Examiner*—Carlos Azpuru
*Attorney, Agent, or Firm*—Rae-Venter Law Group, P.C.

[57] ABSTRACT

Intraocular devices which are capable of sustained release of a cell proliferation modulating agent, together with methods for their preparation and use, are provided. The intraocular devices are implanted in the tissue, and the drug is released from the intraocular device such that the drug is substantially retained within the implant region. The device may be used to inhibit cellular proliferation around the implant. The device can be provided as a kit, preferably in a form suitable for use.

12 Claims, 2 Drawing Sheets

METHODS AND COMPOSITIONS FOR THE MODULATION OF CELL PROLIFERATION AND WOUND HEALING

CROSS-REFERENCE TO RELATED APPLICATIONS

This application is a continuation-in-part of U.S. Ser. No. 08/329,366, filed Oct. 26, 1994, now abandoned, which disclosure is incorporated herein by reference.

INTRODUCTION

1. Field of the Invention

This invention relates to methods and compositions featuring polymer implants associated with cell proliferation modulating agents. The invention provides for the modulation of cell proliferation and/or wound healing at sites immediately adjacent to the implant and for the inhibition of cell adhesion to the implant itself.

2. Background

The inappropriate proliferation of cells in an organism may lead to a variety of disease states. The particular symptoms will vary depending on the type of proliferative cell and on the location of the cell. These disease states may range from cancerous malignancies when the cell is a cancer cell, to scarring when the cell type is a normal fibroblast, or to a skin disease when the proliferating cell is an epithelial or dermal cell forming a part of the integument or skin.

Proliferation of cells in various tissues of the eye can lead to impaired vision. One such example of impaired vision results from a proliferation of lens epithelial cells which remain associated with the lens capsule following cataract surgery. Specifically, extracapsular cataract extraction for the removal of cataracts frequently is accompanied by an undesired proliferation of lens epithelial cells, resulting in posterior lens capsule opacification. Virtually all pediatric patients and approximately 50% of adult patients undergoing extracapsular cataract extraction develop an opaque secondary cataract within three to five years of surgery.

Various cytotoxic agents are reported to inhibit secondary cataract formation or posterior lens capsule opacification. For example, cytotoxic agents such as 5-fluorouracil, methotrexate, colchicine, and daunomycin have been instilled into the anterior chamber of the eye to kill residual lens epithelial cells for prevention of posterior lens capsule opacification. These drugs have been delivered, e.g., by injection or with the aid of various drug delivery techniques that provide for diffusion of the drug within the eye.

A second example of vision-threatening cellular proliferation occurs following glaucoma surgery. Glaucoma encompasses a heterogeneous group of eye diseases characterized by a classical triad of symptoms: elevated intraocular pressure (IOP), optic nerve damage and progressive visual field loss. The increase in IOP is due to a decrease in the outflow of aqueous humor, the fluid in the anterior segment of the eye that is responsible for maintaining pressure balance for the entire eye. Current medical therapy tier glaucoma involves the administration of one or more ocular agents, including beta-blockers (e.g., timolol), miotics (e.g., pilocarpine), adrenergic agonists (e.g., epinephrine) and carbonic anhydrase inhibitors (e.g., acetazolamide). While most glaucoma patients initially respond to drug therapy, many become refractory over time. For those individuals, maintenance of normal IOP requires surgical intervention.

Surgical techniques for the correction of glaucoma include various types of glaucoma filtering surgery (GFS), during which a drainage channel is created for aqueous humor outflow from the anterior chamber in order to lower IOP. The most successful GFS is that which uses the creation of a filtering bleb or drainage fistula, which is an elevation of the conjunctiva at the surgical site, to decrease IOP. Numerous techniques may be employed to maintain the patency of the bleb or fistula, including the use of biocompatible plastic tubes or valves, yet scarring over of the drainage channel frequently causes blockage of the bleb or fistula and a concomitant increase in IOP. Recent clinical studies have demonstrated that introduction of agents which inhibit the wound healing process can in some instances improve the success rate of GFS. These agents typically are administered by non-specific means such as application by sponge to the drainage filter tissue during the surgical procedure or by repeated, painful injections into the conjunctiva after the operation.

Drug delivery techniques which have been reported both for prevention of secondary cataracts and for GFS rely to a greater or lesser extent upon diffusion of the administered drug to the target cell site. However, the continuous movement of the aqueous fluid through the anterior chamber of the eye can alter the effective concentration of the drug at the target cell site. Thus, these delivery techniques create undesirable side effects due to the inherent activity of the modulating agent on cells other than target cells combined with the lack of specific localization to the target site, resulting in a lower effective dose at that site. For example, the non-specific delivery of potent antiproliferative agents such as mitomycin C and 5-fluorouracil often has resulted in inadequate wound healing, leakage of the aqueous humor, hypotony or very low pressure leading to further complications.

It therefore would be of interest for treatment regimens which involve a surgical procedure and for which a successful outcome depends on the modification of cell proliferation, for example, inhibition of growth of lens epithelial cells in cataract surgery and fibroblasts in glaucoma filtering surgery, to identify methods and compositions for the delivery of agents capable of modulating cell proliferation and modulating wound healing responses in a site specific manner.

Relevant Literature

Heyrman, et al. (1989), *J. Cataract Refract. Surg.*, 5: 169, describes studies of drug uptake and release by polymethylmethacrylate (PMMA) and hydrogel intraocular lenses. European Patent Application 0 443 809 A2 describes an intraocular lens (IOL) coated with a hydrophilic material and including a pharmacologically active agent. U.S. Pat. No. 4,918,165 describes an antibody-cytotoxin conjugate covalently linked to an IOL. U.S. Pat. No. 4,170,043 describes an IOL coated with a biocompatible, water-soluble film. U.S. Pat. No. 4,240,163 describes an IOL coated with a medicament.

Biodegradable microcapsules for use in the eye are disclosed in Wong (U.S. Pat. No. 4,853,224). A bioerodible polymer disc containing an aqueous mixture of mitomycin is disclosed by is disclosed by Charles et al. (1991), *Ophthalmology* 98(4): 503. A biodegradable ocular implant for delivery of therapeutic agents is described by U.S. Pat. No. 4,863,457, by Lee et al. (1988), *Invest. Opth. & Visual Science* 29(11): 1692 and by Lee et al. (1987) *Ophthalmol-* ogy 94: 1523. Kay et al. (1986) *Ophthalmic Surgery* 17(12): 796 describe a collagen sponge containing 5-fluorouracil for ocular use. A wafer having a diffusion limiting membrane and containing colchicine is described by Legler, et al. (1993), *J. Cataract Refract. Surg.* 19: 462. See also Hartmann, (1990) *Ophtalmologie,* 4: 102.

The following references also may be relevant to the subject invention: Xu, et al. (1993), *Ophthal. Surgery,* 24(6): 382–388; Tahery and Lee (1989), *J. of Ocular. Pharm.,* 5(2): 155–179; Palmer (1991) *Ophthalmology,* 98: 317–321; K. Mosbach (Editor ed. 1976), *Methods in Enzymology,* Vol. 24 Immobilized Enzymes; S. Wong (1991) *Chemistry of Protein Conjugation and Crosslinking* CRC; G. Pietersz (1990), *G. Bioconjugate Chem.* 1: 89; W. J. Power, et al. (1994), *J. Cat. Refract. Surg.* 19: 440; M. Weller, et al. (1988), *International Ophthalmology* 12: 127; M. Bruce Shields, *Textbook of Glaucoma* (3rd ed. 1992), Ch. 34 and 36; and H. Alkock and F. W. Lampe ( ed. 1981), *Contemporary Polymer Chemistry.*

SUMMARY OF THE INVENTION

The present invention provides methods and compositions for modulating the proliferation of target cells, for example in the eye. The composition is a polymer implant associated reversibly with a cell growth modulating agent. The polymer releases the modulating agent so as to maintain the concentration of the unbound modulating agent substantially within a localized tissue region, so that it affects primarily target cells in the localized region. The invention also provides for an intraocular device comprising a biologically inert polymer associated reversibly with a modulating agent, and methods for preparing the intraocular device. The methods and compositions find use, for example, in the prevention of secondary cataract, in enhancing the success of glaucoma filtering surgery, and in the enhancement of biocompatibility of tissue implants by use of an antiproliferative agent as the cell proliferation-modulating agent to modulate growth of cells migrating into the implant site.

DESCRIPTION OF THE SPECIFIC EMBODIMENTS

Figure 1:
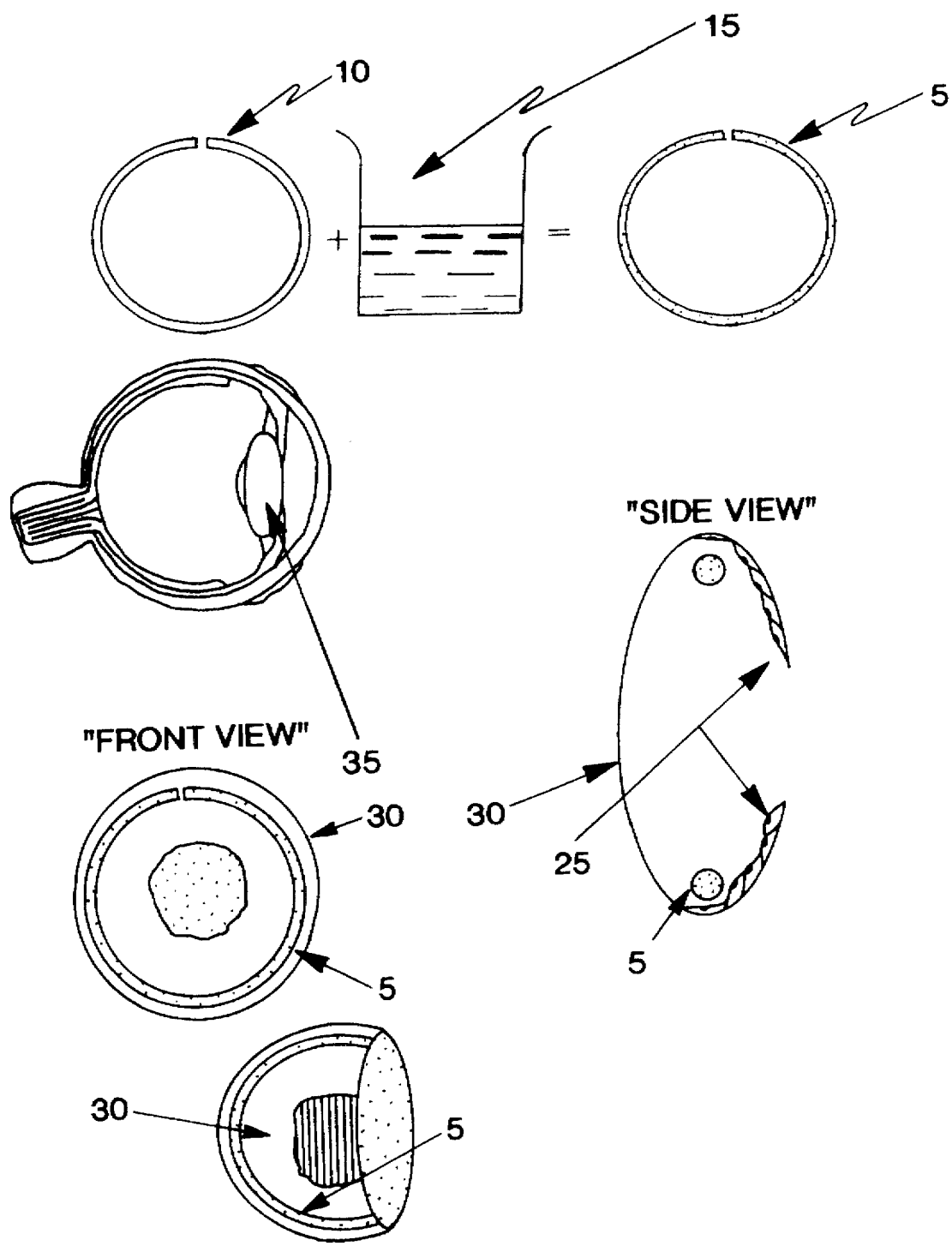
FIG. 1 shows a schematic representation of one embodiment of the invention wherein a tissue of interest is contacted with an implant composed of a polymer and a cell proliferation-modulating agent. In this embodiment, daunomycin (15) is associated with the polymer nylon which has been fabricated as a loop (10) to produce a daunomycin coated loop (5). The daunomycin coated loop (5) is inserted into the lens capsule (30) of the lens (35) following cataract surgery, thus placing the drug in close proximity to the lens epithelial cells (25) which line the inner surface of the capsule (30).
Figure 2:
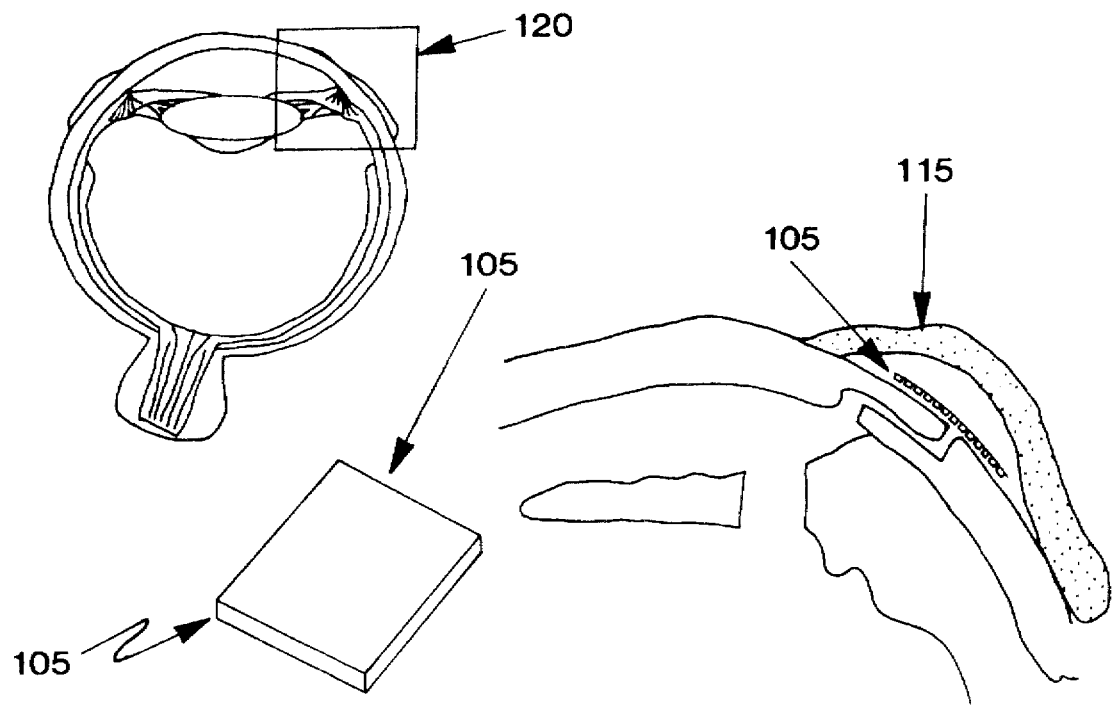
FIG. 2 shows a schematic representation of another embodiment of the invention wherein the cell proliferation-modulating agent daunomycin (15) is associated with a nylon membrane (100) to produce an implant form (105). The nylon-daunomycin implant (105) is contacted with tissue posterior to the conjunctiva (115) in the surgically created fistula (120) following filtration surgery. Implantation at this site places the cytotoxic agent in close proximity to proliferating fibroblasts which in the absence of treatment can cause scarring over of the surgically created drainage channel (120).
Figure 2:
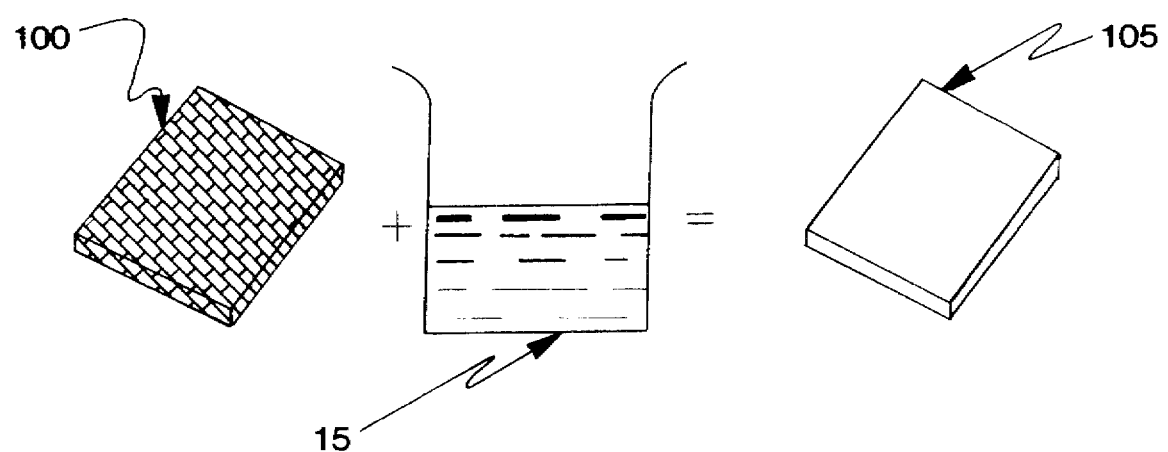

The present invention provides methods and compositions for modulating cell proliferation and wound healing in a tissue of interest. In the methods, a tissue of interest is contacted with a composition which includes a cell proliferation-modulating and/or wound healing agent and a biologically inert polymer implant. The selected modulating agent is associated reversibly with the polymer implant so as to provide for localized delivery of the agent following implantation of the device into the tissue. By "polymer implant" is meant a polymer in a physical form suitable for placement within the body by surgical or other means. The actual physical shape of the polymer implant will be determined by the intended use. The polymer implant can be prepared by immersing the implant into a solution of a modulating agent, whereby the agent is adsorbed to the polymer by hydrophobic/hydrophilic action and/or by chemical linkage. In use, the polymer implant and associated agent are introduced into the tissue during or following surgery. For GFS, the implant is laid on top of the sclerostomy site (if partial thickness) in the subconjunctival space. For prevention of secondary cataracts, the implant is inserted into the lens capsule. The modulating agent is continuously released from the implant polymer at a concentration and rate sufficient to modify cell proliferation and/or wound healing of the target cells in the immediate vicinity of the implant and so have minimal or no effect on cells away from the implant site. The target cells include lens epithelial cells, in the case of secondary cataracts, and fibroblasts and leukocytes, in the case of GFS or any other application in which scarring is to be minimized.

The localized region of modulation will be determined by the release characteristics of the polymer and the concentration of the modulating agent, and can readily be optimized using the experimental techniques described herein. For example, for use in secondary cataract prevention, the implant will reside within the remaining lens capsule, and the modulating agent will be substantially localized to the equatorial region. Localization may be further facilitated when, during normal healing, cells surround and attach to and/or encase the implant. Generally, the localized region will be within 10 mm of the implant, more preferably 7 mm, most preferably 5 mm or less. The modulating activity of the implant will be maximally exerted upon any cell coming into actual contact with the implant. Such contact inhibition is particularly desirable for GFS.

The compositions and methods of the subject invention offer several advantages over currently available methods for modulating cell proliferation and/or wound healing. For example, as a result of binding of the modulating agent to a polymer implant, the modulating agent remains localized in the wound site, creating a high local concentration of the agent and minimizing or eliminating diffusion or systemic delivery to other areas. Even if there is some diffusion away to other areas, the concentration of the antiproliferative agent generally will be insufficient to effect cells in those other areas. In contrast, currently available methods of applying antiproliferative agents without localization can result in complications such as poor control of the proliferation and/or healing and wound leaks and negative effects on cells away from the implant site. Other advantages of the subject invention include control of the dosage of the modulating agent and prevention of unwanted effects on essential cells in the tissue of interest, since localization of the drug to the tissue site prevents migration to other areas of sensitive cells, especially normal cells, and instead sequesters the growth-modulating agent in the region of invading cells. It also is unnecessary to prepare separate formulations for each tissue of interest as the localization of the drug is accomplished by the implant. The resulting effect can, as appropriate, range from complete elimination of an undesirable cell type to inhibition of cell proliferation at the implant site, or could be used to stimulate growth, for example, of a poorly healing wound, such as in a diabetic or a burn patient.

The compositions include a biocompatible polymer implant with which a modulating agent is associated. By "modulating agent" is meant any compound that alters the growth or development of cells, including both cell-proliferation-modulating agents and agents that affect wound healing. Examples include antimetabolites and cytotoxins which kill cells, antimitotics that further inhibit growth or proliferation of cells, growth factors which stimulate cell division, differentiation, etc., or compounds which alter the wound healing process, e.g. by selectively inhibiting or stimulating a population of cells associated with wound healing, such as fibroblasts.

When the intended application is an inhibition of cell proliferation and/or prevention of wound healing, specific proliferation-modulating agents can include daunomycin, daunorubicin, doxorubicin, mitomycin C, 5-fluorouracil, cytosine arabinoside, colchicine, cytochalasin B, bleomycin, vincristine, vinblastine, methotrexate or the like. Also of interest are toxic agents which may be derived from microorganism or plant sources. Examples include naturally occurring toxins such as ricin, abrin, diphtheria toxin, and the like. When the desired result is enhanced cell proliferation or wound healing, the proliferation-modulating agent can be a growth-promoting agent such as fibroblast growth factor, epidermal growth factor, transforming growth factor β, and platelet-derived growth factor and/or the like.

The polymer is biologically inert and physiologically compatible with tissues, e.g., the eye. The polymer also desirably is in and of itself does not induce an inflammatory response. The polymer also preferably is capable of associating reversibly with a sufficient amount of the selected modulating agent, and of releasing that agent in a suitable manner to satisfy the intended objective, e.g., inhibition of wound healing. The preferred characteristics of the polymer include capacity for interacting in a reversible manner with the cytotoxic agent, whereby the cytotoxic agent is released slowly into the eye. The polymer is capable of absorbing the cytotoxic agent either covalently or non-covalently. Examples of association include by way of electrostatic charge, hydrophobic or hydrophilic interactions, or covalently.

Various molecules which have the desired characteristics can be used to prepare the general class of polymers such as polyamides, polypeptides, polyesters, polycarbonates, polyurethanes, polyacetals, polysaccharides, and polyolefins may be used for preparing the polymer implant. Specific examples of such polymers include, but are not limited to, silicone rubber, polyurethane rubber, polyethylene, polyvinyl chloride, poly(hydroxyethyl methacrylate), poly(methyl methacrylate), poly(ethylene terephthalate), polypropylene, polystyrene, poly(tetrafluoroethylene), polyglycolic acid, cellulose, ethylcellulose, methycellulose, dextran, hyaluronic acid, nylon and collagen. Additionally the polymer implant may be a copolymer, composite or blend of the above.

Of particular interest are biologically inert polymer implants with which the modulating agent is associated covalently or noncovalently and coated on the implant in an amount sufficient to provide the desired amount of modulation of cell proliferation following release of the modulating agent after insertion of the implant. One such example is a nylon polymer implant to which is adsorbed an amount of daunomycin sufficient to inhibit cell proliferation and/or wound healing. The nylon polymer to which the cell modulating agent is bound can be in the form of a membrane, or alternatively, the polymer can be in the form of a powder, which can be prepared as a wafer or other implant form by various techniques, i.e., pressure mold. Various fillers/binders and coatings could be used. Essentially the binder would dissolve in aqueous solution allowing the dispersion of the particles. In tissue this would provide a more amorphous distribution than an intact implant. The biological properties of many other suitable polymers are known to the art. The ability to reversibly associate a modulating agent with the polymer is readily determined by one skilled in the art for any polymer having otherwise desired biological properties using methods known to those skilled in the art.

It is desirable for the modulating agents to be bound reversibly to the polymer implant so as to be only locally diffusible about the region in contact with that implant, thereby increasing the local concentration of the modulating agent, while reducing side effects to cells away from the implant site and frequency of administration. The rate of release of the growth-modulating agent from the polymer may vary depending on the particular use. Generally, the rate is about 25 to 50% of the initial amount released in the first 24 hours, and 5–10% per 24 hour period, thereafter.

The polymer implant can be prepared in a number of ways. For example, the modulating agent can be associated with the implant by immersing it in a solution of the modulating agent, whereby the agent becomes reversibly associated with the polymer. The modulating agent also may be reversibly bound to the implant by other coating techniques known to those skilled in the art, such as spraying the implant or flowing the modulating agent about the implant. Two systems are of particular interest. The first system uses a cytotoxic agent (daunomycin, doxorubicin, etc.) absorbed onto the polymer, i.e., nylon. In aqueous solutions daunomycin is released from the nylon slowly. In the second system Imine derivatives of the C-13 carbonyl group of doxorubicin and daunomycin, such as hydrazones and semicarbazones, are suitable for release of drug from polymers since hydrolysis of these types of carbonyl derivatives are known to be acid catalyzed. An article which speaks of these types of bonds is Yamamoto, et al., J. Medicinal Chem. (1972) 15: 872–875.

For covalent linkage of an anti-proliferative agent to the polymer, reactive sites such as —OH, —COOH, —SH or —NH2 can be present on the polymer backbone, or can be introduced by procedures known to those skilled in the art. Where the polymer is nylon, for example, a functional carboxyl group can be introduced by controlled hydrolysis using 3M HCl which also gives an amino group which can be converted to a carboxyl group using succinic anhydride. See, for example, Mosbach, *Methods in Enzymology* and Wong, *Chemistry of Protein Conjugation and Crosslinking*. Of particular interest are linkers that provide covalent bonding of the agent to the polymer such that the bonds can be cleaved enzymatically or by acidic or reducing conditions. Numerous methods for linkage of drugs to the above reactive sites are known to those skilled in the art. See, for example, Pietersz (1990), *Bioconjugate Chem.* 1: 89. Of particular interest for use as cell modulating agents are compounds such as daunomycin that have a carbonyl group capable of forming a hydrazide linkage.

The biocompatibility of the implants can be increased, for example, by attachment of PEG. Methods for preparing activated PEG are well known. See, for example, Bergstrom et al., (1992), *J. Biomed. Mat. Research* 26: 779–790. Methods for preparing polymers with functional groups capable of reacting with these activated PEG molecules are well known. Examples of improved biocompatibility of implant materials with PEG have been published. Such a modification also allows for use of polymers which would be otherwise suitable for use in preparing an implant, but which are not biocompatible, or have poor biocompatibility. Other means of improving the biocompatibility of implants include the use of heparin (see, for example USDN Behar-Cohen et al. (1995) Investigative Ophthalmology Visual Science 36: 5802 which discloses heparin coated IOLs).

The polymer implant can be provided in a variety of forms. It may be a stand-alone device such as IOL, or can be used in conjunction with another device such as an IOL. The polymer can be cast, molded or fabricated into any form suitable for the particular application. For use in the prevention of secondary cataract, for example, the form of the implant can be a substantially circular ("O") ring or loop capable of fitting into the lens capsule in conjunction with the IOL. Such a device has approximately the diameter of the lens and is placed in the eye so as to go around the inner periphery of the capsule. After the device is in place, an IOL is then inserted. Alternatively, for GFS, a thin membrane or sponge is advantageous. A thin polymeric membrane also can be used to encapsulate a polymeric or other implant, when it is desirable that scarring in the region of that implant be minimized.

The load capacity of the polymer for the modulating agent is determined in part by the surface area of the implant and in the case of covalent bonds, by the number of available reactive groups. Accordingly, implants with maximized surface areas, for example porous or woven implants, may be preferred. The implant also may be formed so as to provide a physical gate to cell encroachment, e.g., a lip, ridge, or grid, that is designed to increase physical contact of the target cells with the implant. For example, in GFS the implant can be a membrane which can be implanted in the fistula. The membrane implant generally is designed to allow free passage of aqueous fluid from the filtration site, and generally is of a size to cover the scleral surgery site. An approximate diameter of 1 cm, and a thickness of 1–5 mm, is typical for a membrane implant. The membrane can be placed directly over the scleral surgery site, under the conjunctiva, and hence help support the fistula bleb created during GFS. The implant also can be cut to the shape of and be placed in the scleral bed in the case of a partial thickness surgery.

In use, the polymer implant and associated agent are introduced into the tissue during or following surgery. As an example, for GFS, the polymer implant is placed at the surgical site as follows. The conjunctiva is carefully dissected anteriorly to the limbus. Excessive tenons tissue overlying the sclera are excised. A limbal groove is made and extended anteriorly, into the corneal stroma. Before the anterior chamber is entered, a paracentesis is made through peripheral clear cornea away from the filtering site. Then the anterior chamber is entered through the filtering site and a small (1×3-mm) block of scleral tissue and trabecular meshwork is excised. The edges of the sclerectomy are cauterized to control hemostasis. Then a peripheral iridectomy is performed. The cylindrical polymer is inserted into the sclerostomy site before closure. The implant is fabricated as desired, sterilized by any acceptable means, for example, autoclave (steam) sterilization, irradiation, gas, etc. It is then aseptically immersed into a sterile solution of cell proliferation modulating edgened and dried. It could be air dried, hydrolyzed, etc. and packaged. Nylon powder could be sterilized as above, added to solution of daunomycin for example and dried. It could then be mixed with appropriate formulation agents (such as HPMC, sucrose, etc.) as binders and formed into tablet, wafer, etc. When placed in tissue, the binder would dissolve leaving the nylon-daunomycin particles trapped in the tissue. The drug is slowly released from the particles.

Following insertion of the implant, the cell proliferation-modulating or wound healing agent is continuously released from the implant polymer at a concentration and for a time sufficient to modify cell proliferation or wound healing in the immediate vicinity of the implant. The implant may exhibit a slow, steady-state release of the modulating agent such that the agent remains substantially within the region of the implant. Alternatively, the implant may exhibit a multiphase release in which the polymer delivers an initial "burst" of short duration followed by sustained release of lower concentrations. Such a release profile also advantageously minimizes the amount of modulating agent delivered to non-target regions while advantageously exposing the target cells in the localized region to an initial exposure that rapidly initiates the desired modulation. The load bound to the support depends on the surface area of the support and the concentration of the cell modulating solution and the time. Using high concentrations, a higher amount of weakly associated drug may come as a burst. The amounts can be varied and the release modified by how extensively the implant is washed prior to use. The implant also advantageously retains sufficient concentrations of the desired modulating agent to effectively exert contact modulation upon any target cell physically contacting the implant, for at least several days following placement of the implant.

Thus, both concentration and the release rate of the growth-modulating agent can affect the time elapsed before the effect on target cells is achieved. Generally, the effect on cell proliferation of the cell-modulating agent associated with the implant polymer is realized within 24 to 48 hours after target cells come in contact with the cell-modulating agent, depending upon the concentration of the agent used. The effect may be expected to last as long as 3–5 days or longer, depending upon the release characteristics of the polymer and the potency of the modulating agent.

The effectiveness of the implant with associated cell modulating agent for its intended use can be determined in a variety of ways. Many types of cells can be used to test the complex, preferably cells similar to the cell type in the tissue of interest. For example, when the intended use of the implant is in human ocular tissue, it is preferable that human scleral fibroblast cells obtained from surgical specimens or fresh eye bank tissues are used. When the intended use is a veterinary one, it is preferable that the cells be from the intended recipient host species. For example, when the desired effect is inhibition of cell proliferation, particularly proliferation of cells which migrate into an ocular wound, the implant can be tested an in vitro cell culture assay in which mammalian cells are added to culture wells containing the polymer implants. An in vivo model of the intended condition for treatment, such as glaucoma or secondary cataract development can be used. As an example of an in vitro assay for determining the ability of the conjugate to inhibit or stimulate cell proliferation in vitro. Alternatively, growth can be evaluated by functional determination such as the effect of the test agent on protein synthesis. For example, the stimulation of collagen formation can be monitored in vitro using the incorporation of 1-[2,3-³H]-proline into collagenase susceptible protein. (Peterkofsky, B., et al., (1982) *Immunochemistry of the Extracellular Matrix Vol. II*, ed. Furthmayr, H. CRC Boca Raton, Fla. pp. 19–42.)

In one particular use of the polymer implant, the tissue(s) of interest are the sclera and conjunctiva of the eye, and the intended application of the invention is to enhance the success of glaucoma filtering surgery. In glaucoma filtering surgery, a drainage fistula or channel is surgically created to increase aqueous humor outflow as a means of lowering IOP. The intended application of the polymer implant in glaucoma filtering surgery is to control or down-regulate the healing of the surgical wound such that it heals, but in the process does not create excessive scar tissue to block the filtering channel or bleb that has been made. Since many of the cells in the tissue abutting the wound site are amitotic (non-dividing), the antimitotic agents would have little or no effect on these cells, thus conferring additional selectivity to the use of the implant.

A sufficient amount of the modulating agent on the polymer implant is introduced into the surgical wound site to achieve the desired effect of enhanced healing or inhibition of healing following surgery. An effective concentration is defined as the dose which inhibits cell proliferation using an in vitro assay such as that described above by at least 70%, preferably more than 80%, and most preferably by more than 95% when compared to control plates, i.e., those to which polymer implant alone is added, or as the dose that stimulates cell proliferation by at least 50%, preferably more than 100%, and most preferably by more than 200% when compared to control plates. An effective dose of the conjugates for inhibiting wound healing in GFS generally is in the range of 1–50 µg, more preferably 1–20 µg, still more preferably 1–10 µg.

In another use of the invention, the tissue(s) and cells of interest are the lens capsule and any associated residual lens epithelial cells following cataract surgery. The invention is used to prevent growth of the residual lens epithelial cells on the lens capsule after removal of a primary cataract. The primary cataract can be of any type, including senile, juvenile and radiation-induced. The polymer implant may inhibit proliferation of, or preferably kill, lens epithelial cells which can grow across the optic axis of the posterior lens capsule following removal of the primary cataract. For evaluation of the efficacy of the invention for use in the prevention of secondary cataract following primary extracapsular cataract surgery, an art accepted in vitro model can be used. Cataract surgery is performed in a host animal such as a rabbit according to methods described by Ulrich, et al., ((1993) *J. Cat. Refract Surg.* 19: 462). Following surgery, a polymer implant is inserted into the capsular bag. The implant is crafted in the form of an open loop or ring whose diameter approximates the lens equatorial diameter. Both ends of the loop are placed inside the bag using techniques common for placement of intraocular lens haptics. Various concentrations of the cell proliferation-modulating agent are absorbed to the implant. Following surgery, eyes are observed to determine the effect of the implant on lens epithelial cells proliferating on the posterior capsule surface. At selected times following surgery, animals are humanely sacrificed and the eyes are submitted for histological evaluation to assess the degree of lens epithelial cell proliferation.

The development of secondary cataract in humans can take from a few months to several years. Clinically, secondary cataract is determined by slit lamp microscopy presenting as the appearance of lens epithelial cells growing on the posterior lens capsule (posterior capsule opacification). This opacification, especially if centrally located, can result in decreased visual acuity. Treatment of posterior capsule opacification is conventionally performed by YAG laser capsulotomy which removes the opacified capsule and restores a clear line of vision resulting in improved visual acuity. The invention described herein would, when implanted at the time of primary cataract surgery, allow for the release of therapeutic concentrations of agents cytotoxic for lens epithelial cells. These agents would destroy the cells and hence prevent their proliferation. Thus, slit lamp microscopy can be used to determine that posterior capsule opacification has not occurred. Alternatively, since posterior capsule opacification can lead to a loss of visual acuity, the maintenance of visual acuity at post-cataract surgery levels or a decreased incidence of YAG capsulotomies can be used to determine the efficacy of the implant.

The subject compositions can be provided as kits for use in one or more operations. Kits may include a separate polymer implant and growth-modulating agent. The agent may be a concentrate, including lyophilized compositions, and may be provided in vials which may include one or more dosages. Conveniently, single dosages may be provided in sterilized containers. Alternatively, the kits may include a composition prepared for direct use. Generally, the growth-modulating agent is combined with the solid support by assembly of the various components in a sterile environment and the assembly is maintained in an aseptic environment until use. The compositions are preferably stored dried or lyophilized in a sterile container. Excipients may be used to promote stability under these conditions. Generally if the drug is currently stable under these conditions, it should be stable under the same conditions when associated to an implant. We could just prevent it by maintaining dry conditions. The implant should be kept dry until it is ready for implantation.

The following examples are offered by way of illustration and not by way of limitation.

EXAMPLES

TABLE OF CONTENTS

Example 1 Cytotoxic Activity of Ricin Associated with Polystyrene

Example 2 Release Characteristics of Ricin Associated with Polystyrene Culture Wells Example 3 Binding and Release Characteristics of $^{125}$I-Ricin and Various Polymers Example 4 Cell Proliferation on Daunomycin Associated Nylon Membrane
Example 5 Cytotoxic Activity of Daunomycin Associated with Different Polymers
Example 6 Quantitation of Daunomycin Binding to Different Types of Polymers
Example 7 Binding and Release Characteristics of Daunomycin with Nylon Membranes
Example 8 Nylon-Daunomycin Implant for the Prevention of Secondary Cataracts in a Rabbit Model
Example 9 Nylon-Daunomycin Implant for Control of Scar Formation After Filtering Surgery in Beagles With Glaucoma
Example 10 Covalent Coupling of Daunomycin to Polymer Implant Via a Hydrazone Linkage
Example 11 Binding and Release of Daunomycin from Nylon Powder Example 12 In Vitro Evaluation of Cell Growth Modulating
  Properties of Implants
Example 13 Evaluation of Implant for Enhancement of Cell
  Proliferation During Wound Healing

EXAMPLE 1

Cytotoxic Activity of Ricin Associated with Polystyrene

Ricin (Sigma Chemical Company) was diluted in phosphate buffered saline (PBS) to prepare a dilution series of 20, 2.0, 0.2, 0.02 and 0.002 ug protein/ml. Ricin dilutions were added to duplicate wells (0.5 ml/well) of a 24 well polystyrene culture plate (Corning). PBS was added to two additional wells as controls. Following incubation for 1 hour at 37° C. and overnight at 4° C. the plates were washed three times with PBS to remove all unbound ricin. ME 180 cells (ATCC No. HTB suspended in 1.0 ml M199 (Gibco) containing 10% fetal bovine serum were added to the wells to give $1.0 \times 10^4$ cells/well and incubated at 37° C. for eight days. Following incubation the culture media was aspirated from the wells and cell monolayers stained by the addition of 0.5 ml crystal violet solution (5% in 70% methanol) to each well. Following incubation for five minutes the plates were washed with water to remove excess stain and allowed to air dry. Plates were then inspected with an inverted microscope and the degree of cell growth (percent confluence) was estimated. Results are shown in Table 1, below.

TABLE 1

| Cell Proliferation in Polystyrene Culture Wells Pretreated with Ricin | |
|---|---|
| Pretreatment Concentration (µg/ml)[1] | Percent Cell Confluence[2] |
| 20 | 0 |
| 2.0 | 0 |
| 0.2 | <25 |
| 0.02 | 50–75 |
| 0.002 | 25–50 |
| PBS Control | 50–75 |

[1]Concentration of ricin in PBS added to culture wells.
[2]Percent confluence was estimated by visual inspection of the stained monolayer using an inverted microscope. Zero percent confluence indicates that no cells were observed growing in these wells. One hundred percent confluence would indicate that the well was completely covered with a monolayer of cells.

Thus, this example demonstrates that a modulating agent such as ricin associates with a polymer such as polystyrene and inhibits the growth of cells that contact the coated polymer or are in the vicinity of the polymer implant.

EXAMPLE 2

Release Characteristics of Ricin Associated with Polystyrene Culture Wells

Ricin (Sigma Chemical Company) was diluted in phosphate buffered saline (PBS) to prepare a dilution series of 10, 5.0, 2.5, 1.25 and 0.62, 0.31 and 0.15 µg protein/ml. Ricin dilutions were added to wells (0.5 ml/well) of a 24 well polystyrene culture plate (Corning). PBS was added to additional wells as a control. Following incubation for 1 hour at 37° C. and overnight at 4° C. the plates were washed five times with PBS to remove all unbound ricin. Following washing, 1.0 ml PBS was added to each well and the plate was incubated at 4° C. for 24 hours. Supernatants from individual wells were collected and titrated in a MTT cytotoxicity assay using ME 180 cells. The amount of ricin released into PBS was determined by comparing the cytotoxicity to that obtained with known amounts of ricin. Results are shown in Table 2, below.

TABLE 2

| Binding and Release of Ricin from Polystyrene Cell Culture Wells | |
|---|---|
| Concentration of Ricin Added (ug/ml) | Amount of Ricin Released (ng)[1] |
| 10.0 | 26.2 |
| 5.0 | 12.2 |
| 2.5 | 8.3 |
| 1.25 | 4.6 |
| 0.62 | 4.2 |
| 0.31 | 2.3 |
| 0.15 | 0.84 |

[1]Amount of ricin released from polystyrene following 24 hours incubation in PBS.

Thus, this example demonstrates that the polymer slowly releases the bound modulating agent.

EXAMPLE 3

Binding and Release Characteristics of $^{125}$I-Ricin and Various Polymers

Ricin was labeled with $^{125}$I and diluted to a concentration of 10 ug/ml with a specific activity of $5.8\times10^4$ cpm/ug protein. Polymer balls (¼ inch diameter) were purchased from Polysciences and sterilized by autoclaving. Polymer balls were added to the solution of ricin and incubated at 37° C. for one hour and 4° C. overnight. Following incubation unbound ricin was removed by washing the balls with PBS. Individual balls were added to tubes and the amount of associated radioactivity determined by counting in an LKB compugamma counter. Individual balls were also placed in individual wells of a 24 well culture dish containing 1 ml of M199 containing 10% FBS and $4.5\times10^4$ ME 180 cells. Plates were incubated at 37° C. for five days. Following incubation the individual balls were removed from the wells, rinsed and counted for radioactivity. Aliquots of culture media was collected and counted. The remaining media was then aspirated and the wells stained and inspected as described above.

TABLE 3

| | Ricin Associated with Polymer Balls[4] | | |
|---|---|---|---|
| Polymer | Pre-Incubation[1] (ng/ball) | Post-Incubation[2] (ng/ball) | Percent Confluences[3] |
| Polystyrene | 0.677 | 0.397 | 0 |
| Poly-propylene | 1.004 | 0.598 | 0 |
| Acrylic | 0.192 | 0.143 | 0 |
| Polyamide | 0.161 | 0.081 | 0 |

[1]Ricin associated with polymer balls (nanograms/ball) following rinsing and prior to being added to cell culture wells.
[2]Ricin associated with polymer balls (nanograms/ball) after 5 days of culture in wells
[3]Relative estimation of viable cells attached to cell culture well. Zero indicates no cells.
[4]Controls (balls with no ricer) had percent confluence of 3+.

EXAMPLE 4

Cell Proliferation on Daunomycin Associated Nylon Membrane

Nylon membrane discs (Biodyne A, 7.5 mm in diameter, Pall Biosupport) were cut from sheet membrane using a hole punch and autoclaved. The discs were then incubated in a solution of daunomycin (200 ug/ml in PBS) for two hours at room temperature. Discs were visibly red due to the absorbed daunomycin. The discs were rinsed in PBS and placed in M199 and incubated for an additional 2 and ¾ hours. The discs were finally rinsed and blotted to remove excess liquid. The discs were then placed in the bottom of a 24 well culture plate and ten microliters of ME 180 cells suspended in M199 containing 10% FBS was placed in the center of the disc. Plates were incubated at 37° C. for one hour to allow for cell adhesion and then washed to remove unbound cells. M199 containing 10% FBS was added and the plates incubated at 37° C. for 48 hours. To determine the extent of cell proliferation 1uCi $^3$H-thymidine was added to each well and the plates incubated for an additional 24 hours. The discs were then rinsed in ice cold 10% trichloroacetic acid, rinsed in water and placed in scintillation fluor for counting. Results are presented in Table 4, below.

TABLE 4

Cell Proliferation on Daunomycin Associated Nylon Membranes

| Daunomycin used for Membrane Treatment[1] | Daunomycin in Culture Media[2] | $^3$H-Thymidine Incorporation (cpm[3]) |
|---|---|---|
| − | − | 1627 + 689 |
| − | + | 62 ± 57 |
| + | − | 29 + 4 |

[1]Nylon membrane discs were incubated in a solution of daunomycin in PBS and washed to remove unbound daunomycin. Control membranes were treated with PBS.
[2]Following addition of cells control wells received an aliquot of daunomycin in solution sufficient to inhibit cell proliferation.
[3]Incorporation of $^3$H-thymidine into DNA was used to monitor cell proliferation. Data represent the mean and standard deviation of triplicate values.

EXAMPLE 5

Cytotoxic Activity of Daunomycin Associated with Different Polymers

Polymer balls (¼ inch diameter) were obtained from Polysciences. Individual balls (sterilized by autoclaving) and were placed in a solution of daunomycin diluted to 0.5 mg/ml in PBS and incubated overnight at room temperature. The balls were then rinsed extensively with PBS to remove unbound daunomycin. Individual balls were then placed in wells of a 24 well culture plate (Costar). Additionally a polymethmethylacrylate (PMMA) intraocular lenses (IOL) was treated in a similar manner. A single cell suspension of ME180 cells was prepared by trypsinization of a confluent monolayer and resuspended in M199 containing 10% FBS. One milliliter of cell suspension ($1.4 \times 10^4$ cells/ml) was added to each well of the culture plate. The plate was incubated at 37° C. until control wells (no balls) reached confluence. At this time the media was aspirated and cell monolayers were stained with crystal violet as described above. The degree of cell growth was determined by visually inspecting the wells for stained cells using an inverted microscope. No cells were observed in any of the wells which contained the daunomycin treated polymer balls or the daunomycin treated IOL. In contrast, wells not containing polymer balls or LOLS had a confluent monolayer of growing cells. This example demonstrates that a polymeric IOL may advantageously be treated with a modulating agent to prevent undesired cell growth on or around the IOL.

EXAMPLE 6

Quantitation of Daunomycin Binding to Different Types of Polymers

Polymer balls (¼ inch diameter) were incubated in a solution of daunomycin as described above. Following incubation and rinsing to remove unbound daunomycin individual balls were placed in one milliliter of methanol to extract bound drug. The absorbance of the methanol extracts was read at 476 nm. Using the extinction coefficient of 173 at 1 cm for a 1% solution of daunomycin and the surface area of the balls the capacity of the polymers was determined. Results are shown below in Table 5, below.

TABLE 5

Capacity of Different Polymers for Binding Daunomycin

| Polymer | Daunomycin bound ($\mu g/cm^2$) |
|---|---|
| Polyamide ball (nylon) | 1.26 |
| Polypropylene ball | 0.50 |
| Polystyrene ball | 0.71 |
| Acrylic ball | 0.28 |

This example demonstrates that a variety of polymers will bind daunomycin, with nylon demonstrating superior binding capabilities.

EXAMPLE 7

Binding and Release Characteristics of Daunomycin with Nylon Membranes

Nylon membrane (Biodyne from Pall) discs, diameter 7.0 mm, were cut from sheet membrane using a punch and autoclaved. The discs were then incubated in a solution of daunomycin (Sigma), 50 µg/ml in PBS, for three hours at room temperature. Discs were visibly red in color from the absorbed daunomycin. The discs were thoroughly rinsed with PBS to remove unbound daunomycin. Four discs were added to tubes containing one ml of methanol to extract the bound daunomycin. Daunomycin concentration was determined by measuring the absorbance of the methanol solution at 476 nanometers and an extinction coefficient of 173 for a 1% solution. Eight discs were added to tubes containing one ml of PBS and incubated for 24 hours at room temperature. Following incubation the PBS from tubes containing four of the discs was removed. These discs were extracted with methanol to determine the amount of drug bound to the discs as described above. Incubation of the other four discs was continued for an additional 72 hours (total of 96 hours in PBS). Following incubation the PBS was removed and the discs extracted with methanol to determine the amount of drug bound. Results are shown in Table 6, below.

TABLE 6

Release of Daunomycin from
Nylon Membrane Over Time

|  | Nylon Associated Daunomycin (μg/disc) |
|---|---|
| Initial membrane | 16.5 |
| Following 24 hour PBS Extraction | 10.3 |
| Following 96 hour PBS Extraction | 6.5 |

[1]Total daunomycin (ug) associated per nylon membrane disc. Daunomycin was obtained by extracting from membrane with methanol. Concentration determined by absorbence at 476 nm using 173 (1cm) as the extinction coefficient for a 1% solution of daunomycin.

EXAMPLE 8

Nylon-Daunomycin Implant for the Prevention of Secondary Cataracts in a Rabbit Model Secondary cataract typically develops in rabbits within a few weeks following cataract surgery as indicated by proliferation of residual lens epithelial cells on the posterior lens capsule. The effect of a nylon loop-daunomycin implant on the proliferation of lens epithelial cells following cataract surgery is evaluated in vivo in a rabbit model.

Cataract surgery is performed according to methods described by Ulrich, et al., ((1993) *J. Cat. Refract. Surg.* 19: 462). Female New Zealand white rabbits are randomly assigned to two treatment groups of six animals per group. Both groups receive lens extraction surgery with phacoemulsification in one eye. The surgical procedure simulates the method used on humans to remove primary cataracts. Animals in group 1 will receive untreated nylon loops. Animals in group 2 receive nylon loops to which one of the test concentrations of the cell proliferation-modulating agents is absorbed. Loops are placed inside the lens capsule following removal of lens material by phacoemulsification.

All of the rabbits will receive one week of standard post-surgical care involving anti-inflammatory (topical steroid and antibiotic (topical gentamicin) treatment. Eyes are then observed to determine the effect of the implant on lens epithelial cells proliferation on the posterior capsule surface. At selected times (three and six months), animals are sacrificed and their eyes are submitted for histological evaluation to assess the degree of lens epithelial proliferation.

By implanting the subject intraocular nylon-daunomycin implant into the anterior chamber, remnant lens epithelial cells can be inhibited from proliferating, thus preventing secondary cataracts. The use of an intraocular implant provides a superior means for delivery of cytotoxic drug by allowing for release of drug over time and protection of the drug from degradative processes in the eye. The subject methods and device thus provide a simple procedure for preventing secondary cataracts.

EXAMPLE 9

Nylon-Daunomycin Implant for Control of Scar Formation After Filtering Surgery in Beagles With Glaucoma Beagle dogs are naturally susceptible to glaucoma and are well accepted as a model for human glaucoma. King, et al. (1991), *Am. J. Vet. Res.* 52: 2067–2070. Two groups of six beagles each with glaucoma, as characterized by an IOP of greater than 30 mm Hg in one or both eyes receive glaucoma filtering surgery in one glaucomatous eye; one group receives nylon membrane-daunomycin implant and the other group is treated with nylon filter control. Beagles will be given a preoperative eye examination with a Zeiss slit lamp biomicroscope. Preoperative IOP will be obtained from the average of three measurements by pneumototometry, using an Applanation Pneumatograph (BioRad), after the installation of one drop of 0.5% proparacaine HCl to each eye. The dog is placed under general anesthesia, a lid speculum placed, a limbal-based conjunctival portame is made approximately 8 mm posterior to the limbus and sharp and blunt dissection performed until the cornea scleral limbus is well visualized. A triangular partial thickness scleral flap is then developed based at the limbus to approximately 50% scleral depth, and then an entry wound into the anterior chamber is made with a sharp 15 degree razor knife. A 1 mm×3 mm sclerostomy is then performed to excise the tissue under the partial thickness flap. A peripheral iridectomy is performed with Vannus scissors and curved jewelers' forceps. The sclera flap is sutured in place with 10-0 nylon suture. A nylon membrane coated with daunomycin is then laid between the sclera and conjunctiva. The conjunctiva is closed with a running absorbable suture.

The animals are then given a combination antibiotic/steroid ointment applied to each eye, are kept warm, and observed every hour for eight hours and then every four hours the following day. Daily observations continue thereafter with the instillation of the antibiotic steroid ointment for approximately 21 days. Examinations including a routine ophthalmic examination for bleb patency, toxicity and complications, slit lamp biomicroscopy and pneumotonometry, are performed daily for the first five days after surgery, then every third day through week six, and then weekly through week twelve. Observations, including variations in IOP, are subjected to standard statistical analysis to look for maintenance of lowered IOP.

EXAMPLE 10

Covalent Coupling of Daunomycin to Polymer Implant Via A Hydrazone Linkage

Nylon membrane discs (Biodyne C, pore size 1.2 micron, 7 mm diameter, Pall Biosupport) having free carboxyl groups were immersed in 30 ml of adipic acid dihydrazide (100 mg/mL in water). One-ethyl-3-[dimethylamino)-propyl]carbodiimide (EDC) was added to the solution to a final concentration of 3.0 mg/ml and the membrane discs were incubated for 90 minutes at room temperature. The pH was maintained at 4.75 by the dropwise addition of 1.0M HCl. Following incubation, the membrane was washed extensively with water and added to a solution of daunomycin (3.0 ml, 2.0 mg/ml) in 0.2M sodium acetate buffer pH 4.5 and incubated for 48 hours at room temperature. Following incubation, the membrane discs were rinsed with PBS to remove unassociated daunomycin. The membrane discs were placed in 100% methanol (1 ml/disc) for 2 hours to remove noncovalently bound daunomycin. A total of 37.2 μg/disc was removed by this procedure. The discs were placed in a 1:1 solution of methanol and 0.2M sodium acetate buffer pH 4.5 (1 ml/disc) and incubated at room temperature to extract daunomycin bound to nylon via the hydrazone linkage. After 24 hours, the discs were removed and the extraction buffer saved. The discs were placed in 1 ml of fresh extraction buffer. The amount of daunomycin released into the extraction buffer was determined spectrophotometrically. This process was repeated at 48 and 96 hours.

In the first 24 hours 37.4 µg/cm² was released. At 48 hours an additional 12.15 µg/cm² was released. At 96 hours an additional 8.6 µg/cm² was released. A total of 58.2 µg/disc was extracted. Following the above incubations, the discs were slightly red, indicating that some daunomycin was still associated with the nylon. Control membranes that did not receive the hydrazide treatment also bound daunomycin. Substantially all of the daunomycin was removed from these discs during the initial methanol extraction.

EXAMPLE 11

Binding and Release of Daunomycin from Nylon Powder

Nylon 6 pellets (Polysciences Inc., 3 g) were suspended in 100 ml of % 100 methanol containing 20% $CaCl_2$. Following extended incubation (four days) with stirring at room temperature, the nylon solution was added dropwise with stirring into a large excess (2 liters) of water at room temperature. The powder thus obtained was separated on a suction filter and washed successively with water and absolute ethanol and dried under vacuum.

Nylon powder (15.5 mg) was weighed out and ground in a mortar. The powder was added to a 0.5 ml solution of daunomycin (2.2 mg/ml) in PBS and incubated overnight at room temperature. Following incubation, the powder was washed twice with PBS by centrifugation to remove unbound daunomycin. The daunomycin associated powder was resuspended in 1.0 ml of methanol and incubated overnight at room temperature. Following incubation, the methanol was recovered and the powder extracted two more times. The concentration of daunomycin in the extraction solutions was determined spectrophotometrically. The total daunomycin extracted per mg of nylon powder was 51.9 µg.

EXAMPLE 12

In Vitro Evaluation Of Cell Growth Modulating Properties of Implants

Polymer implants coated with agents that modulate cell proliferation can be evaluated in vitro. Cell culture wells are loaded with one ml M199 medium containing 10% FBS. The implant polymer coated with cell proliferative agent is added to the wells. Culture wells are then seeded with cells from the tissue of interest, for example, scleral or conjunctival-derived fibroblasts or lens epithelial cells, and incubated for a sufficient time with the growth-modulating composition to observe the desired effect. Growth is determined for each plate by any method known to those skilled in the art, such as trypan blue dye exclusion, tritiated thyroidine incorporation and the like. Cell growth also can be determined by direct microscopic visualization of cells, either stained or unstained. Alternatively cell growth can be determined using the vital dye MTT (3-(4,5-dimethylthiazol-2y)-2,5-diphenyl tetrazolium bromide. This dye is converted to a blue formazan product by living cells, but not dead cells (Mosman, *J. Immunol. Methods* (1983) 65: 55). The blue product is then solubilized with sodium dodecyl sulfate/HCl and quantitated on an ELISA reader at 590 nm. The $IC_{50}$ value is determined by the concentration of agent that causes killing of 50% of the cells compared to the untreated control wells.

EXAMPLE 13

Evaluation of Implant for Enhancement of Cell Proliferation During Wound Healing The polymer implant with associated cell proliferation modulating agent can be evaluated in any of a number of art accepted wound healing models. Especially relevant in this instance are models which incorporate surgical wounds. The polymer implant, coated with cell proliferation modulating agent, for example, transforming growth factor type beta (TGF type beta), is placed subconjunctivally in rabbit eyes. New Zealand white rabbits are placed under general anesthesia and a lid speculum is placed in the eye. A limbal based conjunctival flap is created by incision of the conjunctiva and blunt dissection forward to the limbus. Care is taken not to cut the episclera. The implant is placed under the flap and the conjunctiva is closed with 9-0 vicryl suture in a running-looking fashion.

Animals are sacrificed on days 3, 5 and 7 following implantation. The eyes are enucleated and fixed in neutral buffered formalin. Paraffin sections of tissue containing the implant are prepared, followed by staining with hematoxylin and eosin to observe the degree of fibrovascular proliferation at the implant site. Staining of sections with Massons trichrome is performed to observe newly formed collagen fibers at the implant site. The degree of fibrovascular proliferation and the amount of newly formed collagen in and around the implant is substantially greater in tissue receiving implants coated with TGF type beta as compared to implants with no agent or tissue not receiving an implant.

The above examples thus demonstrate that modulating agents such as ricin and daunomycin reversibly associate with polymers such as polystyrene, polypropylene, acrylic, polyamide, and nylon. The modulating agent is then released by the polymer. The association and release can be readily determined using the above experimental methods. The polymer can be crafted into an implant form suitable for the desired application and implanted into an animal. The method can be applied to prevent secondary cataracts or to maintain patency of a filtering bleb in GFS.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for modulation of proliferation of target cells in a localized region of the eye, said method comprising:

contacting said localized region with a polymer implant with which is reversibly associated a modulating agent, wherein said modulating agent is released from said polymer implant into said localized region at a rate such that said modulating agent primarily affects target cells in said localized region of the eye as compared to cells outside said localized region.

2. The method according to claim 1, wherein said target cells are lens epithelial cells.

3. The method according to claim 1, wherein said target cells are fibroblasts.

4. An intraocular device comprising:

a biologically inert polymer which is reversibly chemically associated with a proliferation modulating agent.

5. The device according to claim 4, wherein said proliferation modulating agent is daunomycin.

6. The device according to claim 4, wherein said biologically inert polymer is nylon.

7. The device according to claim 6, wherein said nylon is a powder.

8. A method for killing residual lens epithelial cells in an eye following cataract surgery, said method comprising:

implanting an intraocular device comprising a biologically inert polymer associated reversibly with a proliferation inhibiting modulating agent into the anterior or posterior chamber of said eye, so that said proliferation inhibiting agent kills substantially all of said residual lens epithelial cells.

9. A method for preventing formulation of scar tissue in a region, said method comprising:

implanting a device comprising a biologically inert polymer associated reversibly with a modulating agent into said region, wherein said modulating agent inhibits the growth of fibroblasts in said region and thereby prevents said formation of scar tissue.

10. The method according to claim 9, wherein said region is an ocular filtration site.

11. The device according to claim 4, wherein said proliferation modulating agent is ricin.

12. The device according to claim 4, wherein said biologically inert polymer is polymethylmethacrylate.

* * * * *